United States Patent [19]

Kaiser

[11] 3,996,017
[45] Dec. 7, 1976

[54] CASSETTE SEPARATING COLUMN SYSTEM FOR CHROMATOGRAPHY

[76] Inventor: Rudolph E. Kaiser, Dr. Dahlem Strasse 9, Bad Durkheim 6702, Germany

[22] Filed: Nov. 23, 1973

[21] Appl. No.: 418,277

[30] Foreign Application Priority Data

Nov. 24, 1972 Germany .......................... 2257575

[52] U.S. Cl. .................................. 23/292; 23/259; 23/253 R; 23/232 C; 73/23.1; 210/31 C
[51] Int. Cl.² ................. B01D 15/08; G01N 31/04; G01N 31/06
[58] Field of Search ................. 23/232 C, 259, 297, 23/253 R; 210/31 C; 73/23.1

[56] References Cited
UNITED STATES PATENTS

| | | | |
|---|---|---|---|
| 3,167,396 | 1/1965 | Staunton et al. | 23/259 X |
| 3,443,416 | 5/1969 | Webb | 55/386 |
| 3,527,567 | 9/1970 | Philyaw et al. | 23/232 C X |
| 3,682,315 | 8/1972 | Haller | 210/198 C X |
| 3,897,679 | 8/1975 | Guild | 73/23.1 X |

OTHER PUBLICATIONS
Lab Crest Chromatographic Columns, Cat. No. 80A270, 10/6/66.

*Primary Examiner*—Morris O. Wolk
*Assistant Examiner*—Michael S. Marcus

[57] ABSTRACT

A chromatographic system including cassettes, each containing a separating column which is connected at each of its ends to a coupling piece having both of its ends in the form of conical surfaces on the outside of the cassettes. These conical coupling surfaces may be connected to complementary-shaped conical fittings in a fluid-tight manner to connect the inlet and outlet ends of the column of the chromatographic instrument lines such as, for example, the sample injector, stream splitter, backflushing inlet and outlet lines, detector and auxiliary gas flows. A special connection fitting allows the direct connection of the conical coupling surfaces of two column-containing cassettes, as well as connection to other parts of the chromatograph between the columns. Thus, the separating column cassettes may be utilized as components of various relatively simple and complex chromatographic systems.

7 Claims, 7 Drawing Figures

CASSETTE SEPARATING COLUMN SYSTEM FOR CHROMATOGRAPHY

This invention relates to a mechanical system for the easy installation, connection, switching and changing of packed and capillary separating columns in gas and liquid column chromatography.

It is known that the present technique of installation, connection, switching and changing of separation (column) systems in gas and liquid column chromatography using fluid-tight tube connections presents stringent requirements on the nature and quality of the mating surfaces and on the skill and know-how of the user. The reason for this is the stringent requirements of said chromatographic techniques on the tightness, geometry (e.g., alignment) and dead-volume of such connections. The accomplishment of chemically correct (i.e., inert,) temperature-resistant and mechanically safe connections with the exchange of, glass columns (both packed and capillary) in particular is so difficult that many persons are restricted as to the possibility of using this technique in their work.

It is known that gas-and liquid-tight connections for chromatography columns often utilize one or more gaskets in screw joint; the packings of the fittings are adversely affected by temperature changes and many times these become unusable after only a single use in case of stringent requirements. Moreover, screw joints can be secured correctly only by the use of tools which requires that thermostatting ovens be undesirably voluminous in order to afford sufficient working space. Glass columns require plastic packings which need to be inserted on precision-formed glass parts and are deformed irreversibly by the influence of heat glass parts. This fact results in serious restrictions as to construction material.

The aforementioned reasons explain why many of the users of chromatographic apparatus hesitate to break the connections — once they have been made finally tight for gas or liquid — between the separation column system and the instrument, resulting in the elimination of the possibility of desirable switching, changing, and optimization of separation column systems. Thus, the use of separation column systems of glass and quartz in environmental, biochemical or medical-analytical chromatography is rendered difficult.

In addition to the disadvantages already mentioned, both glass and steel separation column systems require mechanically fixed connection ports. Due to the multiplicity of the instrumental dimensions (e.g., distance between connections) a corresponding multiplicity is also needed in the dimensions of the separation column systems.

The object of the present invention is to avoid or eliminate the above mechanical, chemical and munipulative limitations and difficulties and to make the exchange, switching and coupling of separation column systems significantly easier and capable of accomplishment without the need to use tools. In addition, the cassette-type packed and open capillary column assemblies of the invention hereinafter described permit the replacement of an unnecessarily wide variety of column types by one or a few basic types; in this way the comparison of different chromatographic analytical results is made easier.

This problem is solved by constructing the separation column system in the form of a cassette, having conically formed inlet and outlet T-pieces or couplings which can be coupled in a gas-or liquid-tight manner to the inlet and outlet ports or fittings of a chromatographic instrument with the help of mechanical or pneumatic forces, using suitable gaskets, which couplings and fittings automatically center themselves, and which preferably can also be connected to each other without creating any dead volume.

The coupling and connection fittings contemplated by the invention also permit the switching of separation processes according to the known methods, with gases or liquids. The exchange of the separation column system or systems is done simply by reducing or releasing of the coupling pressure and insertion of a new cassette-form separation system or systems.

The T-formed construction of the inlet and outlet of the separation column systems permit the use of all possible coupling or switching processes without introducing any dead volume. This system easily accommodates all of the requirements of capillary chromatography such as stream splitting before the inlet of the capillary, dilution at the outlet and, in the case of programmed temperature operation, the mixing of additional mobile phase behind the separation system and before the detector (to maintain constant total flow to the detector).

An additional advantage of the new system is the ease of use of protective gas flushing at the connecting points as compared with existing systems, since the shape and position of the coupling point is constant and known. This possibility eliminates the destruction of separation column systems particularly sensitive to oxygen or water vapor.

Thus, the individual advantages of the invention are:
1. mechanically simple connection and disconnection of column systems, without the use of tools;
2. the provision of column connections without dead volume and affording freedom of selection as to construction materials and their chemical inertness in accordance with operating requirements;
3. the elimination of screwing or bending manipulation in column installation/exchange and hence the potential for breakage;
4. the provision of a chromatography column connection system which is relatively insensitive to temperature and temperature changes and facilitates protective gas flushing at the coupling point;
5. the facilitation of connection, switching, and application of secondary systems such as stream splitters and auxilary gas or liquid sources.

An example of a separating column cassette assembly of the invention and an example for both relatively simple and complicated application in a chromatograph is illustrated in the drawings in which.

Figure 1:
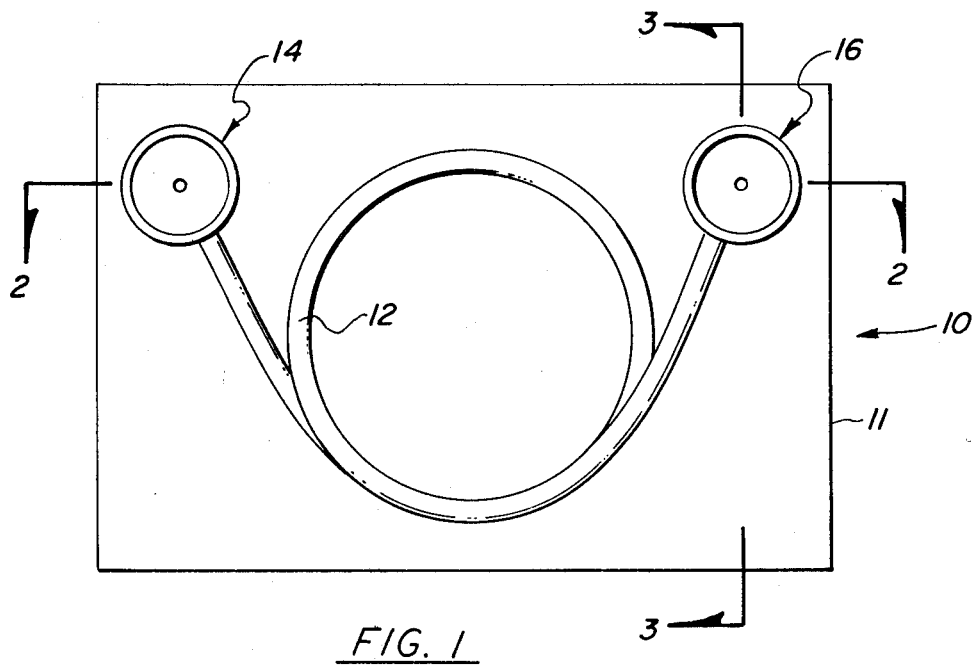
FIG. 1 is an elevational view of a chromatography column cassette with one wall omitted to expose interior details.
Figure 2:
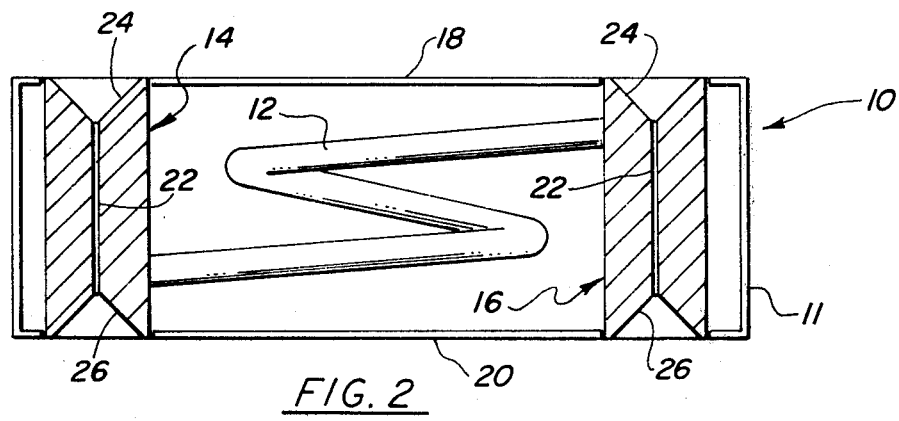
FIG. 2 is a sectional view of the cassette of FIG. 1 taken on line 2—2 looking in the direction of the arrows.
Figure 3:
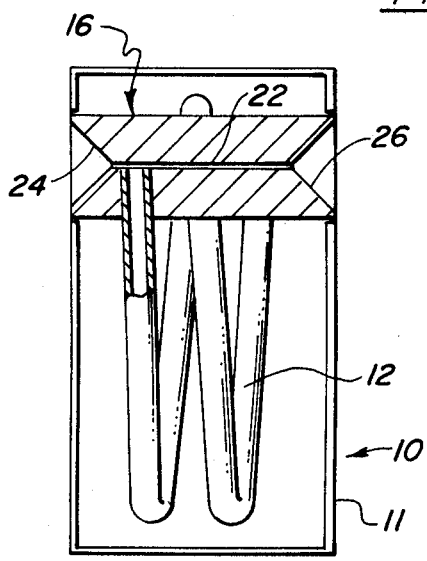
FIG. 3 is a sectional view on line 3—3 of FIG. 1 looking in the direction of the arrows.

In FIGS. 1, 2, and 3, the entire separating column cassette 10 is shown comprising a housing 11; the surface of housing 11 which would be uppermost in FIG. 1 is omitted in that figure to reveal interior details, specifically, a packed or capillary column 12 and a pair of T-pieces or coupling members 14, 16. Each of the respective ends of the column 12 is connected to one of two T-pieces or coupling members 14, 16, which are made of a compact, thickwall tubing and are secured in the cassette housing walls 18, 20.

Each of the coupling members 14, 16 is of essentially cylindrical configuration and contains an axial bore 22 extending therethrough and terminating in respective coaxial conical recesses 24, 26.

Figure 4:
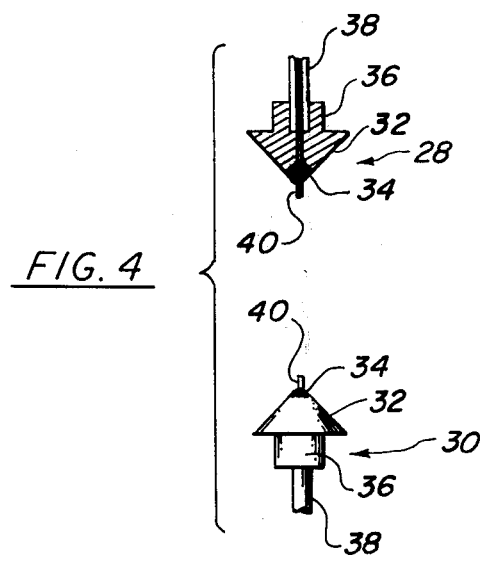
FIG. 4 is a detailed view, partly in section, showing an embodiment of the coupling fittings contemplated by the invention for connection of the column cassette to a chromatography instrument.

Connection of cassette 10 to other separation column systems, if any, to the sample inlet, to the flushing gas and the steering gas, to a stream splitter or a flow restriction, and/or to the detector is accomplished by means of connection fittings 28, 30 as shown in FIG. 4.

In the illustrated embodiment, each fitting 28, 30 comprises a conical portion 32 complementary to, and adapted to be received in, a respective conical recess 24 or 26 in coupling member 14 or 16, as the case may be. The apex of conical portion 32 is formed of packing material 34.

At the base of conical portion 32 and coaxial therewith, each fitting has a reduced diameter hollow cylindrical portion 36 into which is fitted a connection tube 38 for conducting fluid to or from the fitting. A flow passage through the fitting is formed by a hollow needle-like member 40 which projects beyond the apex packing 34 and enters the bore 22 of the respective coupling member 14, 16 when the fittings are pressed into sealing engagement. Hollow needle 40 eliminates any dead volume and also prevents the clogging of the connection by the conical packing 34.

Figure 5:
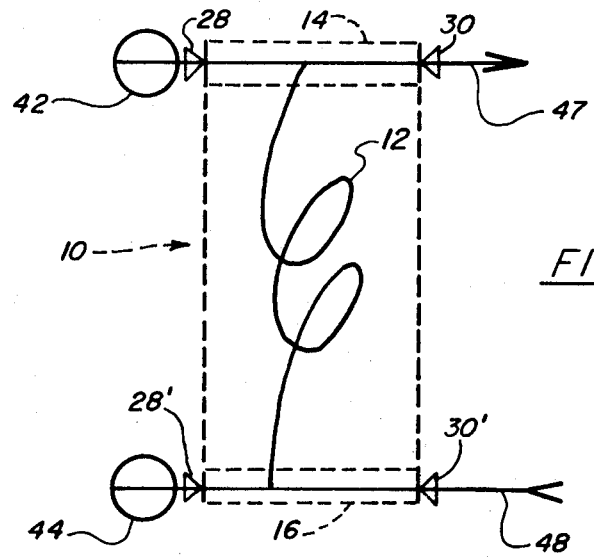
FIG. 5 is a diagrammatic representation of a relatively simple complete chromatographic instrument embodying a cassette column in accordance with the present invention.

FIG. 5 schematically represents the typical application of the cassette system contemplated by the invention. In addition to a cassette 10, containing a chromatograph column 12, this system (schematically illustrated) includes a sample injector 42 and a detector 44. Injector 42 is connected in fluid-tight relation with one end (the uppermost in FIG. 5) of column 12 by means of a connection fitting 28 engaging the lefthand end of a coupling member 14. Similarly, detector 44 is connected in fluid-tight relation with the outlet end (lowermost in FIG. 5) of column 12 by means of connection fitting 28' engaging the lefthand end of a coupling member 16.

A conduit 47 is coupled in fluid-tight relation to the righthand end of a coupling member 14 by a connection fitting 30 and conduit 48 is similarly connected to the righthand end of coupling member 16 by connection fitting 30'. It will be appreciated that coupling members 14, 16 and connection fittings 28, 28', 30 and 30' schematically shown in FIG. 5 may take the physical form of their counterparts shown in and described with reference to FIGS. 1–4. A conduit 46 may lead to a stream splitter (not shown) but may alternatively (or additionally) provide the connection to an outlet backflushing line (not shown). Connection 48 may be the protective gas supply (not shown) for detector 44, a pressure regulator (not shown) for flow adjustment used in temperature programming (to maintain constant flow to the detector) or an inlet connection for backflushing.

Figure 6:
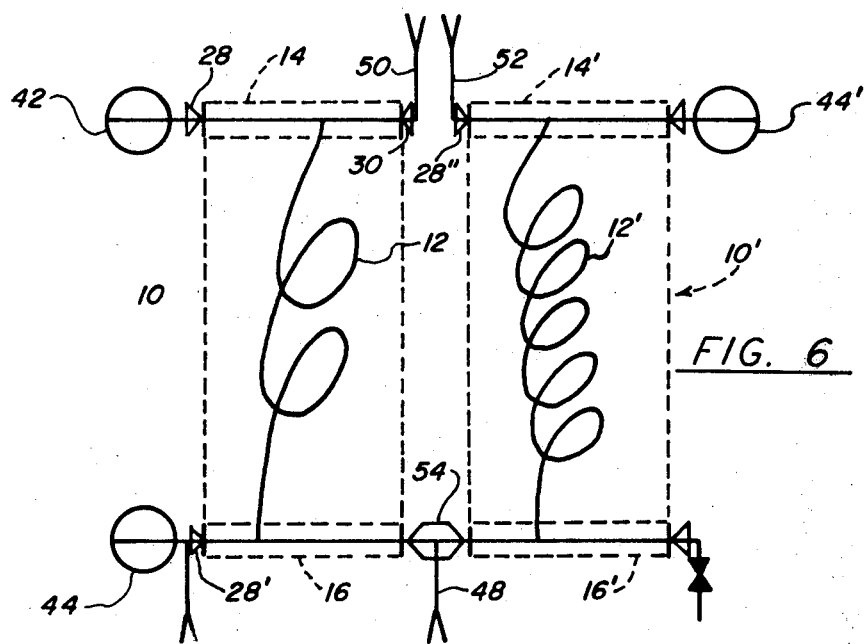
FIG. 6 is a diagrammatic representation similar to FIG. 5 indicating the manner in which two cassettes can be connected relative to the other components of a more complex chromatographic instrument.
Figure 7:
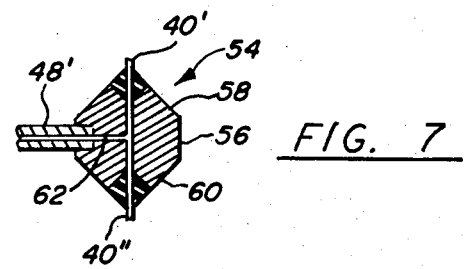
FIG. 7 shows a modified coupling fitting which may be utilized for interconnection of two cassettes for application such as that exemplified by FIG. 6.

FIG. 6 represents a more complex system, i.e., for multiplex chromatography where a plurality of columns are connected simultaneously or in predetermined time sequence. The chromatographic system comprises two cassettes 10 and 10' having respective columns 12, 12'. The cassettes may be identical to each other and to that shown in, and described with reference to, FIGS. 1–3, inclusive. As in the case of FIG. 5, the FIG. 6 system includes a sample injector 42 and a detector 44 coupled to column 12 in the same manner as the correspondingly numbered counterparts in FIG. 5. In addition there is provided a second detector 44' which is connected to the righthand end of the coupling member 14' of cassette 10' and, consequently, to the upper end of column 12'. Four additional flow conduits are provided: an inlet conduit 46 is connected between detector 44 and the lower end of column 12 via a connection fitting and the lefthand end of the coupling member 16 of cassette 10; conduit 48 is connected between the respective lower ends of columns 12 and 12' via connection fitting 54 (shown in detail in FIG. 7 and described presently) and coupling members 16, 16' at the bottoms of the cassettes; conduit 50 is connected to the upper end of column 12 via a connection fitting 30 at the righthand end of coupling member 14; and conduit 52 is connected to the upper end of column 12' via the connection fitting 28'' at the lefthand end of upper coupling member 14'. Where it is necessary to couple two cassettes with a "T" connection, a cassette and a detector or other system component, a connection device such as 54, FIG. 7, may be advantageously employed. Connection fitting 54 comprises a body 56 terminating at opposite ends in identical conical surfaces 58 and 60. The conical surfaces are disposed in coaxial relationship with their respective aspices oppositely directed. Coaxially aligned needle members 40', 40'' extend from the respective aspices of conical surfaces 58, 60 and are in flow communication with an internal T-shaped passage 62 in body 50 to which a flow conduit such as 48' may be connected. If desired, a fitting such as 54 can be provided with two connections for external conduits and with internal passages connecting each external conduit to a respective one of the needle members 40', 40''. Connection fittings of the type exemplified by fitting 54 are installed in a manner wholly analogous to fittings 28, 30 between co-axially aligned coupling members such as 14, 16 disposed with conical surfaces in spaced confronting relation and in engagement with complementary conical surfaces 58, 60 of the connection fitting.

In operation of the FIG. 6 system, the sample is introduced at 42. It is separated in separation column 12 in a first cassette 10 (at left in FIG. 6) and flows to detector 44' as long as no strong mobile phase flow is introduced at 46. Protective or steering gas flows in from at 48. If the flow at 48 is reduced and at 46 increased, then the outlet flow from the (lower end of the) lefthand column (12) is directed through the right-hand column (12') in a second cassette 10' and from there, to detector 44''. Protective or backflushing gases (in the case of gas chromatography) or liquids (in the case of liquid chromatography) may be introduced at 50, while at 52 one can connect a stream splitter or back-flushing flow for the left column. Dilution gas (or liquid), in between a reactor, cooler or condensor, can be switched into the separation line at the connection point of conduit 48 or of conduits 50, 52.

In this way, any desired switching arrangement and connections of one or more separation systems can be carried out easy and safely. The necessary packing tightness will be obtained by application of a constant pressure by adjustable means such as a screw cap, pneumatic pin, etc. directed axially, i.e., along the axes of needle members 40, 40′, 40″.

By proper choice of the construction material (i.e., good thermal conductivity, but of low heat capacity, by using relatively thin walls, etc.) and volume, temperature programming is possible.

Although a specific embodiment has been illustrated and described, various modifications will be obvious to those skilled in the art and may be made without departing from the spirit of the invention. It is intended, therefore that the scope of the invention be limited only as defined in the appended claims.

What is claimed is:

1. A chromatographic column cassette comprising:
 a. a housing;
 b. a chromatographic separating column mounted within said housing;
 c. respective coupling members each with a flow passage therein being located within said housing and being connected to the ends of said column, said flow passage being in communication with the interior of said column and the exterior of said housing, each of said coupling members further having two open ends terminating at the exterior of said housing in conical surfaces lying on a common axis and coaxially adjoining said flow passage, said column being connected to said flow passage at a locus between said two conical surfaces in a non-parallel relationship with respect to said flow passage, said conical surface being disposed adjacent said housing and being accessible from and at the exterior of said housing for receiving and making sealing engagement with a connection fitting having a complementary conical surface.

2. A chromatographic system comprising:
 at least one chromatographic column cassette comprising a housing, a chromatographic separating column mounted within said housing, respective coupling members each with a flow passage therein being located within said housing and being connected to the ends of said column, said flow passage being in communication with the interior of said column and the exterior of said housing, each of said coupling members further having two open ends terminating at the exterior of said housing in conical sufaces lying on a common axis and coaxially adjoining said flow passage, said column being connected to said flow passage at a locus between said two conical surfaces in a non-parallel relationship with respect to said flow passage; and
 connection fittings having complementarily mating conical surfaces sealingly engaging said conical surfaces of said coupling members for establishing flow connections with said separating column within said cassette.

3. A chromatographic system according to claim 2 in which at least one of said coupling members and said complementary connection fittings comprises packing arranged at said conical surface for assuring a fluid-tight flow connection therebetween.

4. A chromatographic system according to claim 3 in which a hollow needle passes through the center of said packing, thereby preventing clogging of the flow connection made by said mating conical surfaces.

5. A chromatographic system according to claim 2, in which at least one of said connection fittings comprises a pair of complementarily mating conical surfaces connected by a flow passage for sealingly engaging conical surfaces of coupling members of two different cassettes so as to provide at least a potential flow connection between the two separating columns within said cassettes.

6. A chromatographic system according to claim 5, in which said flow passage between said pair of complementarily mating conical surfaces of said connection fitting includes a branched flow passage for connecting of a part of the chromatographic system external to said cassettes effectively between the respective separating columns within the two connected cassettes.

7. A chromatographic system according to claim 2, in which said housing and coupling members of said cassette comprise relatively good thermal conducting material and have a relatively low total heat capacity, so as to facilitate the use of temperature programming in said chromatographic system.

* * * * *